United States Patent [19]
Takiguchi et al.

[11] Patent Number: 6,027,718
[45] Date of Patent: Feb. 22, 2000

[54] ORGANOPOLYSILOXANES

[75] Inventors: Osamu Takiguchi; Katsuhiko Rinto; Takashi Oda, all of Wakayama, Japan; Ferdinand Pesch, Darmstadt, Germany; Atsuhiko Ii, Darmstadt, Germany; Christine Cajan, Darmstadt, Germany; Dirk Weichaus, Darmstadt, Germany

[73] Assignee: Kao Corporation, Tokyo, Japan

[21] Appl. No.: 09/035,300

[22] Filed: Mar. 5, 1998

[30] Foreign Application Priority Data

Mar. 6, 1997 [JP] Japan ..................................... 9-051440
Apr. 30, 1997 [DE] Germany ............................ 197 18 185

[51] Int. Cl.[7] ................................ A61K 7/06; A61K 7/00
[52] U.S. Cl. ....................... 424/70.1; 424/401; 424/70.2; 424/70.11; 424/70.12
[58] Field of Search .................................. 424/401, 70.1, 424/70.2, 70.11, 70.12

[56] References Cited

FOREIGN PATENT DOCUMENTS 0 524 612   1/1993   European Pat. Off. .
524612 A2   1/1993   European Pat. Off. .
0 640 643 A2 3/1995   European Pat. Off. .

OTHER PUBLICATIONS

Database WPI, Derwent Publications, AN 92–145623, JP–4–085 335, Mar. 18, 1992.

*Primary Examiner*—Thurman K. Page
*Assistant Examiner*—Lakshmi Channavajjala
*Attorney, Agent, or Firm*—Oblon, Spivak, McClelland, Maier & Neustadt, P.C.

[57] ABSTRACT

Organopolysiloxanes composed of an organopolysiloxane segment and a poly(N-acylalkyleneimine) segment which is bonded to at least one silicone atom of said organopolysiloxane segment via an alkylene group containing heteroatom (s) and which consists of repeating units represented by formula (1):

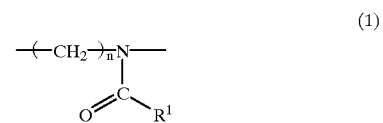

wherein $R^1$ represents a hydrogen atom or an alkyl group having 1 to 3 carbon atoms; and n is a number of 2 or 3;

wherein the weight ratio of the organopolysiloxane segment (a) to the poly(N-acylalkyleneimine) segment (b) [(a)/(b)] is at least 5/95 and less than 40/60, and the weight-average molecular weight is from 10,000 to 500,000.

These organopolysiloxanes are soluble or dispersible in water and can form a film with an excellent texture. Thus, they can be appropriately employed as additives for cosmetic products.

6 Claims, 2 Drawing Sheets

ORGANOPOLYSILOXANES

FIELD OF THE INVENTION

This invention relates to novel organopolysiloxanes. More particularly, it relates to organopolysiloxanes which are soluble or stably dispersible in solvents, in particular, water and, after removing solvents, form a film with an inherent excellent texture of silicone, thus being appropriate particularly as additives for cosmetic products.

BACKGROUND OF THE INVENTION

Because of having various characteristics including low surface tension, good lubricating properties and mold releasing characteristics, high heat stability, low glass transition point and high gas permeability, organopolysiloxanes (hereinafter sometimes referred to as "silicones") have been widely employed in lubricating agents, heat media, electrical insulating materials, leveling agents for paints, mold releasing agents, cosmetic additives, fiber treating agents, shock absorbing materials, sealings, templating agents, glazing agents, foam stabilizers, defoaming agent, etc.

Among these, silicone oils are frequently employed as cosmetic additives in skin care products, foundations, shampoos, hair rinses, hair conditioners, mainly for improving texture. Silicone resins are also used in the form of spherical fine particles in skin care products.

Moreover, film-forming polymers are used in hair setting agents. However, the silicone polymers capable of forming a film would generally undergo crosslinkage via covalent bonding, which restricts the solvent types usable therefor. These silicone bases have another disadvantage that they cannot be easily washed away, when employed in skin or hair care products. On the other hand, hydrophilic silicone emulsions are highly soluble in solvents but cannot form any film capable of imparting an excellent texture.

Organopolysiloxanes having poly(N-acylalkyleneimine) segments are disclosed in EP-524612A, JP-A-3-287509 and JP-A-5-112423. Those publications relate to a polymer compound wherein the weight ratio of the organopolysiloxane segument/the poly(N-acylalkyleneimine) segument is 1/20 to 20/1, and the weight-average molecular weight is 500 to 500,000, for obtaining a modified silicone having characteristics of silicon oils and excellent solubility to polar solvents as well as water.

However, the concrete products disclosed in the above publications are those having a comparatively low molecular weight or having a low content of poly(N-acylalkyleneimine) segument, which can not always provide excellent texture when used for a hair care product.

EP-640643A further discloses that an organopolysiloxane grafted with the same type poly(N-acylalkyleneimine) is soluble in ethanol and can be easily added to hair cosmetics so as to achieve good setting performance. However, this material has no self-dispersibility in water. Even though an aqueous dispersion thereof is formed forcibly, it shows only a poor stability being unsuitable for cosmetics in practice.

SUMMARY OF THE INVENTION

Accordingly, an object of the present invention is to provide organopolysiloxanes which are capable of forming a film imparting an excellent texture while being usable in aqueous preparations and can be easily washed away when employed in skin or hair care products.

Under these circumstances, the present inventors have found out that, among organopolysiloxanes composed of the above-mentioned organopolysiloxane segment and a poly(N-acylalkyleneimine) segment bonded thereto, those having a specific composition and molecular weight are soluble or dispersible in solvent, in particular, water, can form a film with an excellent texture, can be easily washed away and, therefore, are appropriately usable as additives for skin or hair care products.

Accordingly, the present invention provides an organopolysiloxane composed of an organopolysiloxane segment and a poly(N-acylalkyleneimine) segment which is bonded to at least one silicone atom of said organopolysiloxane segment via an alkylene group containing heteroatom(s) and consists of repeating units represented by formula (1):

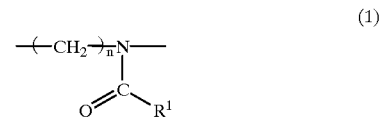

wherein $R^1$ represents a hydrogen atom or an alkyl group having 1 to 3 carbon atoms; and n is a number of 2 or 3; wherein the weight ratio of the organopolysiloxane segment (a) to the poly(N-acylalkyleneimine) segment (b) [(a)/(b)] is at least 5/95 and less than 40/60, and the weight-average molecular weight is from 10,000 to 500,000.

DETAILED DESCRIPTION OF THE INVENTION

Figure 1:
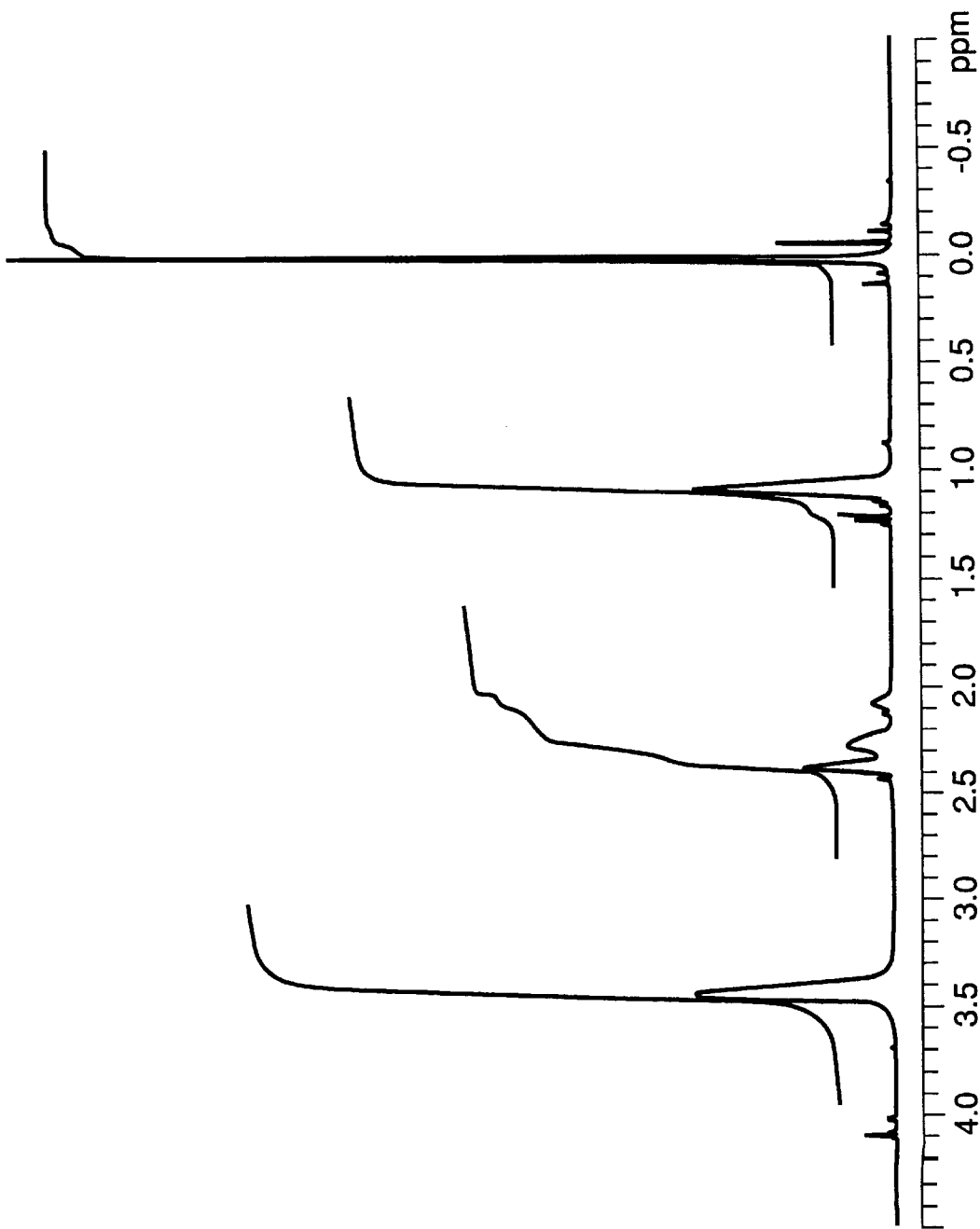
FIG. 1 is a proton NMR chart of the organopolysiloxane A obtained in Example 1.

In the organopolysiloxane of the present invention, the weight ratio of the organopolysiloxane segment (a) to the poly(N-acylalkyleneimine) segment (b) [(a)/(b)] is at least 5/95 and less than 40/60, preferably at least 20/80 and less than 40/60 and more preferably at least 25/75 and less than 40/60, while weight-average molecular weight thereof is from 10,000 to 500,000, preferably from 20,000 to 200,000 and more preferably from 50,000 to 150,000. When this weight ratio (a)/(b) is 40/60 or more or the weight-average molecular weight exceeds 500,000, the solubility of the organopolysiloxane in solvents is lowered. When the weight ratio (a)/(b) is less than 5/95 or the weight-average molecular weight is less than 10,000, the organopolysiloxane can give no inherent excellent texture characteristic of silicones.

As the alkylene group containing heteroatom(s) which mediates between the organopolysiloxane segment and the poly(N-acylalkyleneimine) segment, alkylene groups having from 2 to 20 carbon atoms and containing 1 to 3 nitrogen, oxygen and/or sulfur atoms are exemplified. Concrete examples thereof include alkylene groups having 2 to 20 carbon atoms and containing, between carbon atoms in the alkylene chain and/or at the end thereof, a group of (i) a secondary amine or a tertiary amine; (ii) an ammonium salt formed by adding $H^+$ to a secondary or tertiary amine; (iii) a quaternary ammonium salt; (iv) an oxygen atom; and/or (v) a sulfur atom. Among these alkylene groups, preferable examples are as follows:

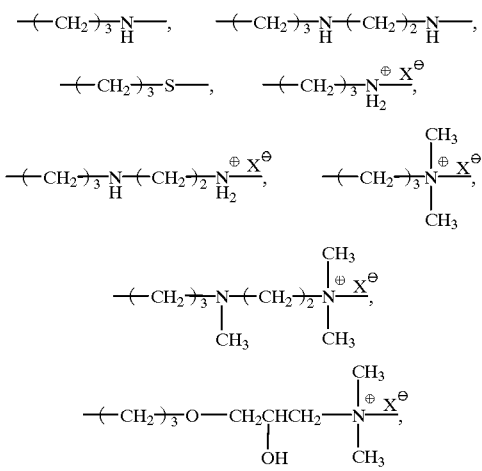

wherein $X^{\ominus}$ represents the counter ion of the quaternary ammonium salt. Examples of the alkyl group $R^1$ having 1 to 3 carbon atoms include methyl, ethyl and propyl groups.

The organopolysiloxane of the present invention is produced by, for example, reacting an organopolysiloxane having functional groups represented by the following formulae:

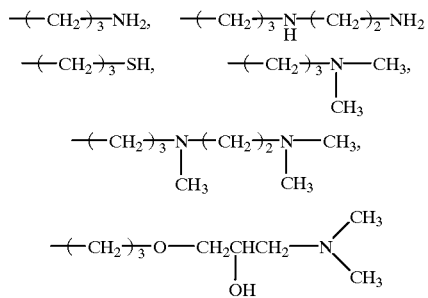

with a terminal reactive poly(N-acylalkyleneimine) obtained by subjecting a cyclic imino ether represented by formula (2) to ring opening polymerization:

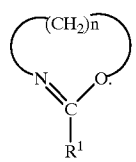

(2)

wherein $R^1$ and n have the same meaning as defined above.

The ring opening polymerization of the cyclic imino ether (2) is performed by using, as an initiator, a highly electrophilic compound, for example, methyl, ethyl, propyl or benzyl esters of strong acids such as benzenesulfonic acid, p-toluenesulfonic acid, trifluoromethanesulfonic acid, trifluoroacetic acid or sulfuric acid. When 2-$R^1$-substituted-2-oxazoline is employed as the cyclic imino ether, for example, then poly(N-acylethyleneimine) [in the formula (1), n being 2] is obtained. When 2-$R^1$-substituted-2-oxazine is employed, then poly(N-acyltrimethyleneimine) [in the formula (1), n being 3] is obtained.

It is preferable that the organopolysiloxane of the present invention is in the form of a solid at ordinary temperatures under atmospheric pressure (usually −10 to 40° C., 1 atm). It is soluble or stably dispersible in solvents, for example, water or lower alcohols ($C_{1-6}$ alcohols) and the dispersion thereof is highly stable. It is particularly preferable that the organopolysiloxane of the present invention is soluble or stably dispersible in water, being capable of giving a dispersion when it is mixed with water at a solid content of 10% by weight and stirred while heating to 80° C.

The organopolysiloxane of the present invention is used especially in hair care products and thus imparts an appropriate texture, conditioning properties, improved combability as well as a natural appearance to the hair treated.

The term "hair care products" as used herein involves, for example, hair-setting agents, shampoos, rinses, treatments and hair dyes in the form of spray, mist, gel, lotion, tonic, blowing agent, cream or post-foaming gel.

The content of the organopolysiloxane of the present invention in the hair care products preferably ranges from 0.05 to 20% by weight, more preferably from 0.1 to 10% by weight.

In addition to the organopolysiloxane and water, the hair care products of the present invention may contain small amounts of solvents such as lower ($C_{1-6}$) alcohols. It is preferred that these alcohols are used in small amounts (i.e., about 1% by weight). Other components commonly employed in hair care products are also used: such as surfactants, oils, polyhydric alcohols, various medicinal components, preservatives and perfumes depending on the purpose, usage and form of each product.

More particularly, the various components, film-forming polymers, propellants, etc. described in EP-640643A can be used.

When the organopolysiloxane of the present invention is used in the hair care products, it is preferable to employ one or more nonionic or ionic polymers therewith.

As the above-mentioned nonionic polymer, use can be made of, for example, "Luviskol" manufactured by BASF AG. The content of the nonionic polymer(s) ranges from 0.1 to 10% by weight, preferably from 0.25 to 5% by weight and more preferably from 0.5 to 3% by weight.

Among the ionic polymers as-described above, examples of cationic polymers include "Gafquat" manufactured by ISP and "Luviquat" manufactured by BASF AG.

Examples of amphoteric polymers include "Amphomer" manufactured by National Starch and "Yukaformer" and "Yukaformer Am 75" manufactured Mitsubishi Chemical Industries, Ltd.

Examples of anionic polymers include "Gantrez AN", "Gantrez ES" and "Gantrez ES 225" manufactured by ISP and "Resyn" manufactured by National Starch.

The content of the cationic, amphoteric or anionic polymer(s) ranges from 0.1 to 5% by weight, preferably from 0.25 to 2.5% by weight and more preferably from 0.5 to 1.5% by weight.

EXAMPLES

To further illustrate the present invention, and not by way of limitation, the following Examples will be given. In these Examples, an organopolysiloxane segment content means a value obtained by determining Si by plasma emission spectrochemical analysis, while a weight-average molecular weight means the average molecular weight in terms of polystyrene determined by gel permeation liquid chromatography with the use of chloroform as the eluent.

Example 1

Synthesis of Organopolysiloxane A

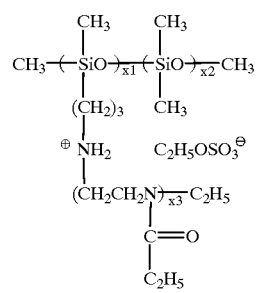

wherein $X_1$, $X_2$ and $X_3$ mean each the number of repeating units and the ratio of $X_1/X_2/X_3$ is 1/33/30.

12.78 g (0.0829 mol) of diethyl sulfate and 246.6 g (2.488 mol) of 2-ethyl-2-oxazoline were dissolved in 519 g of dry ethyl acetate and the resulting solution was heated under reflux in a nitrogen atmosphere for 15 hours to synthesize terminal reactive poly(N-propionylethyleneimine). To the obtained product was added at once 166.7 g (0.0829 mol in terms of amino group) of a 33% solution of branched primary aminopropyl-modified polydimethylsiloxane (molecular weight: 30,000, amine equivalent: 2,010) in ethyl acetate and the obtained mixture was heated under reflux for 12 hours. The reaction mixture was concentrated under reduced pressure to give an N-propionylethyleneimine/dimethylsiloxane copolymer as a pale yellow solid (422 g, yield 99%). This product had a weight-average molecular weight of 108,000. As the result of neutralization titration by hydrochloric acid with use of methanol as the solvent, it was found out that no amino group remained therein.

FIG. 1 shows the proton NMR chart of the organopolysiloxane A thus obtained.

In the organopolysiloxane A, the weight ratio of the organopolysiloxane segment (a) to the poly(N-acylalkyleneimine) segment (b) [(a)/(b)] as will be shown hereinafter was determined from the ratio of the content of methyl groups bonded to Si (corresponding to the area of the peak around 0.1 ppm in NMR) to the contents of ethylene and ethyl groups in (b) (corresponding to the areas of the peaks around 1.1 ppm, 2.2 to 2.4 ppm and 3.4 ppm in NMR).

(a)

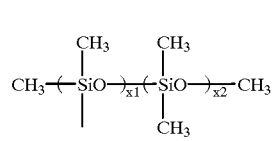

(b)

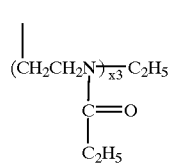

Example 2

Synthesis of Organopolysiloxane B

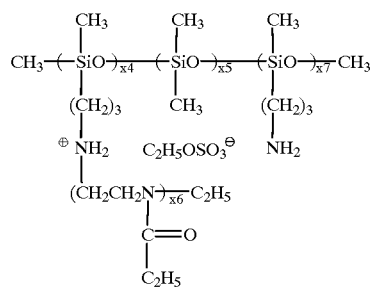

wherein $X_4$, $X_5$, $X_6$ and $X_7$ mean each the number of repeating units and the ratio of $X_4/X_5/X_6/X_7$ is 3/165/150/2.

7.67 g (0.0497 mol) of diethyl sulfate and 246.6 g (2.488 mol) of 2-ethyl-2-oxazoline were dissolved in 519 g of dry ethyl acetate and the resulting solution was heated under reflux in a nitrogen atmosphere for 15 hours to synthesize terminal reactive poly(N-propionylethyleneimine). To the obtained product was added at once 166.7 g (0.0829 mol in terms of amino group) of a 33% solution of branched primary aminopropyl-modified polydimethylsiloxane (molecular weight: 30,000, amine equivalent: 2,010) in ethyl acetate and the obtained mixture was heated under reflux for 12 hours. The reaction mixture was concentrated under reduced pressure to give an N-propionylethyleneimine/dimethylsiloxane copolymer as a pale yellow solid (417 g, yield 99%). This product had a weight-average molecular weight of 154,000. As the result of neutralization titration by hydrochloric acid with use of methanol as the solvent, it was found out that amino groups remained therein at a ratio of 40%.

Example 3

Synthesis of Organopolysiloxane C

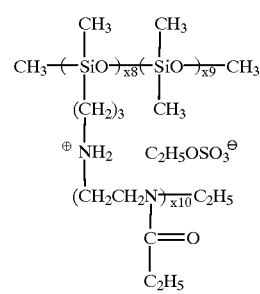

wherein $X_8$, $X_9$ and $X_{10}$ mean each the number of repeating units and the ratio of $X_8/X_9/X_{10}$ is 1/82/75.

5.16 g (0.0335 mol) of diethyl sulfate and 249 g (2.51 mol) of 2-ethyl-2-oxazoline were dissolved in 508 g of dry ethyl acetate and the resulting solution was heated under reflux in a nitrogen atmosphere for 15 hours to synthesize terminal reactive poly(N-propionylethyleneimine). To the obtained product was added at once 166.7 g (0.0335 mol in terms of amino group) of a 33% solution of branched primary aminopropyl-modified polydimethylsiloxane (molecular weight: 40,000, amine equivalent: 4,980) in ethyl acetate and the obtained mixture was heated under reflux for 12 hours. The reaction mixture was concentrated under reduced pressure to give an N-propionylethyleneimine/dimethylsiloxane copolymer as a pale yellow solid (409 g, yield 97%). This product had a weight-average molecular weight of 101,000. As the result of neutralization titration by hydrochloric acid with use of methanol as the solvent, it was found out that no amino group remained therein.

Example 4

Synthesis of Organopolysiloxane D

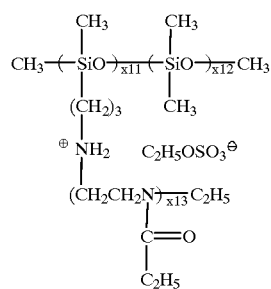

wherein $X_{11}$, $X_{12}$ and $X_{13}$ mean each the number of repeating units and the ratio of $X_{11}/X_{12}/X_{13}$ is 1/33/47.

10.02 g (0.0650 mol) of diethyl sulfate and 385 g (3.88 mol) of 2-ethyl-2-oxazoline were dissolved in 770 g of dry ethyl acetate and the resulting solution was heated under reflux in a nitrogen atmosphere for 15 hours to synthesize terminal reactive poly(N-propionylethyleneimine). To the obtained product was added at once 167 g (0.0831 mol in terms of amino group) of a 33% solution of branched primary aminopropyl-modified polydimethylsiloxane (molecular weight: 30,000, amine equivalent: 2,010) in ethyl acetate and the obtained mixture was heated under reflux for 12 hours. The reaction mixture was concentrated under reduced pressure to give an N-propionylethyleneimine/dimethylsiloxane copolymer as a pale yellow solid (468 g, yield 97%). This product had a weight-average molecular weight of 105,000. As the result of neutralization titration by hydrochloric acid with use of methanol as the solvent, it was found out that no amino group remained therein.

Comparative Example 1

Synthesis of Organopolysiloxane a 30.6 g (0.199 mol) of diethyl sulfate and 945 g (9.53 mol) of 2-ethyl-2-oxazoline were dissolved in 1,950 g of dry ethyl acetate and the resulting solution was heated under reflux in a nitrogen atmosphere for 8 hours to synthesize terminal reactive poly(N-propionylethyleneimine). To the obtained product was added at once 800 g (0.165 mol in terms of amino group) of a 50% solution of branched primary aminopropyl-modified polydimethylsiloxane (molecular weight: 110,000, amine equivalent: 4,840) in ethyl acetate and the obtained mixture was heated under reflux for 12 hours. The reaction mixture was concentrated under reduced pressure to thereby give an N-propionylethyleneimine/dimethylsiloxane copolymer as a pale yellow, rubbery solid (1,720 g, yield 97%). This product had a weight-average molecular weight of 122,000. As the result of neutralization titration by hydrochloric acid with use of methanol as the solvent, it was found out that no amino group remained therein.

Test Example 1

The organopolysiloxanes obtained in the above Examples 1 to 4 and Comparative Example 1 and a commercially available organopolysiloxane x (Silicone Elastomer KE-10, manufactured by Shin-Etsu Chemical Co., Ltd.) were evaluated in solubility-or dispersibility in water or ethanol by the following methods. The results are shown in Table 1.

(Evaluation method)

Figure 2:
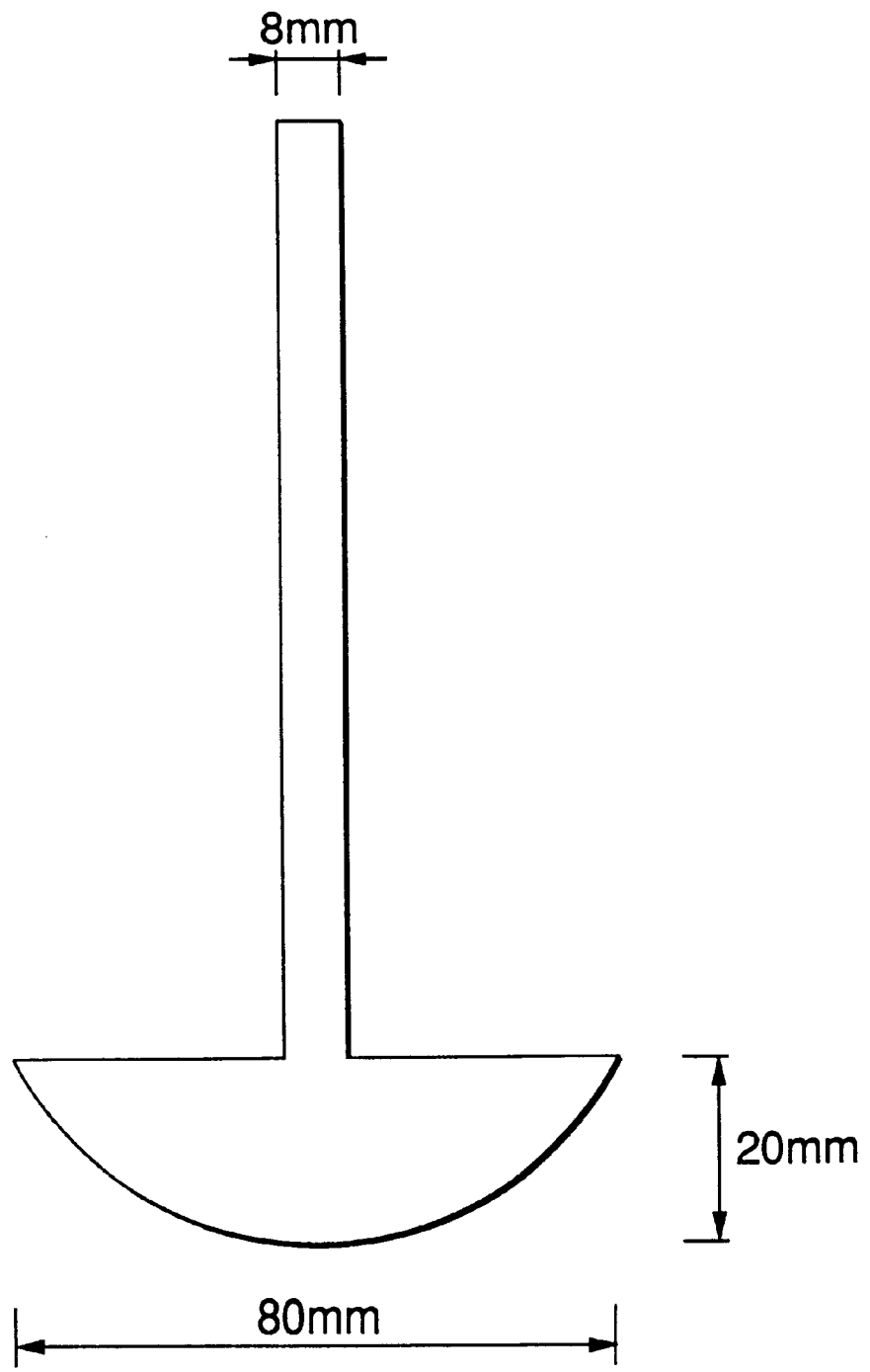
FIG. 2 is a diagram showing a stirring rod employed in the preparation of the dispersion in Test Example 1.

(1) Dispersibility in Water 20 g of each organopolysiloxane was introduced into a 500 ml three-necked separable flask and 180 g of deionized water was added thereto. Next, the obtained mixture was stirred at the bulk temperature of 80° C. for 6 hours and then at 60° C. for 6 hours at 200 rpm by using a Teflon stirring rod as shown in FIG. 2. The aqueous dispersion thus obtained was allowed to stand at room temperature for 24 hours. When the supernatant showed a solid content concentration of 9% by weight or more, the organopolysiloxane was judged as being self-dispersible in water. The solid content concentration was determined by sampling 2 g of the supernatant into a weighing bottle, drying it at 105° C. under 30 Torr for 2 hours and then weighing.

(2) Stability of Aqueous Dispersion

The aqueous dispersions obtained in the above (1) were filtered through a filter paper (ADVANTEC No. 2: manufactured by Toyo Roshi K.K., retention particle size 5 μm) to give samples for evaluating the stability of the aqueous dispersions. Each sample was centrifuged (5,200 rpm, 5 minutes) and the solid content concentration of the supernatant was determined by the same method as described in the above (1). When the supernatant showed a solid content concentration of 9% by weight or more, the aqueous dispersion of the organopolysiloxane was judged as being highly stable after centrifugation.

(3) Freeze Stability of Aqueous Dispersion

Each sample obtained in the above (2) was allowed to stand in a freezer at −25° C. for 24 hours and then brought back to room temperature followed by allowing to stand for 24 hours. Next, the solid content concentration of the supernatant was determined by the same method as described in the above (1). When the supernatant showed a solid concentration of 9% by weight or more, the aqueous dispersion of the organopolysiloxane was judged as having a high freeze stability.

(4) Solubility in Ethanol 10 g of each organopolysiloxane was introduced into a 500-ml three-necked separable flask and 190 g of ethanol was added thereto. Next, the obtained mixture was stirred at room temperature for 12 hours in the same manner as described in the above (1). The obtained solution was allowed to stand at room temperature for 24 hours followed by the determination of the solid content concentration of the supernatant as in the above (1). When the supernatant showed a solid content concentration of 4.5% by weight or more, the organopolysiloxane was judged as being soluble or dispersible in ethanol.

TABLE 1

| Evaluation method | Oorganopolysiloxane | | | | | |
|---|---|---|---|---|---|---|
| | A | B | C | D | a | x |
| Wt. ratio (a)/(b) | 39.4/ | 39.8/ | 39.7/ | 29.7/ | 45.3/ | — |
| | 60.6 | 60.2 | 60.3 | 70.3 | 54.7 | |
| (1) (%) | 9.3 | 9.5 | 9.4 | 9.7 | 9.1 | 0.6 |
| (2) (%) | 9.2 | 9.3 | 9.2 | 9.6 | 9.0 | 0.4 |
| (3) (%) | 9.3 | 9.4 | 9.3 | 9.6 | 6.8 | 0.3 |
| (4) (%) | 4.9 | 5.0 | 5.0 | 5.0 | 4.9 | 0.9 |

As is apparent from the results of Table 1, the organopolysiloxanes of the present invention are each dispersible in water to give a highly stable aqueous dispersion. Also, these organopolysiloxanes are highly soluble in ethanol.

Example 5

By using the organopolysiloxanes obtained in the above Examples 1 to 4 and Comparative Example 1, hair care products (hair foams, hair gels, set lotions, shampoos and rinses) of the following formulations were prepared.

In the case of the shampoos and rinses, the texture of the hair after rinsing was evaluated. In the case of other setting products, the texture of the hair after the evaporation of the solvent was evaluated. These evaluations were each made by 10 panelists.

The organopolysiloxane of Comparative Example 1 was insoluble in water in the formulations 1 to 9 and thus could not be adequately added thereto.

In contrast, the organopolysiloxanes of Examples 1 to 4 imparted each a highly slippery and favorable texture.

Formulation Example 1

| (Pump foam spray) | % by wt. |
| --- | --- |
| Organopolysiloxane | 5.0 |
| Polyquaternium-46 | 3.0 |
| Vinyl pyrrolidone/vinyl acetate copolymer (Luviskol ® VA64) | 2.0 |
| Certrimonium chloride | 1.0 |
| PEG-40-hydrogenated castor oil | 0.1 |
| Perfume | 0.2 |
| Water | ad 100.0 |

Formulation Example 2

| (Pump foam spray) | % by wt. |
| --- | --- |
| Organopolysiloxane | 5.0 |
| Vinyl pyrrolidone/vinyl acetate copolymer (Luviskol ® VA64) | 2.0 |
| Decyl polyglucoside (P.D.:1.5) | 1.0 |
| PEG-40-hydrogenated castor oil | 0.1 |
| Perfume | 0.2 |
| Water | ad 100.0 |

Formulation Example 3

| (Pump hair spray) | % by wt. |
| --- | --- |
| Organopolysiloxane | 15.0 |
| 1,3-Butanediol | 2.0 |
| PEG-40-hydrogenated castor oil | 0.1 |
| Perfume | 0.2 |
| Water | ad 100.0 |

Formulation Example 4

| (Styling aerosol foam) | % by wt. |
| --- | --- |
| Organopolysiloxane | 3.0 |
| Methacrylic acid/ethyl acrylate/tert. butyl acrylate copolymer (Luviskol ® 36D) | 5.0 |
| 2-Amino-2-methyl-1-propanol | 1.1 |
| Ceteareth-25 | 0.3 |
| Laureth-4 | 0.2 |
| PEG-40-hydrogenated castor oil | 0.1 |

| -continued | |
| --- | --- |
| (Styling aerosol foam) | % by wt. |
| Perfume | 0.2 |
| Propane/butane propellant mixture | 10.0 |
| Water | ad 100.0 |

Formulation Example 5

| (Hair spray) | % by wt. |
| --- | --- |
| Organopolysiloxane | 1.0 |
| N-octyl acrylamide/tert-butyl aminoethyl methacrylate/acrylic acid copolymer (Amphomer ®) | 5.0 |
| 2-Amino-2-methyl-1-propanol | 1.0 |
| PEG-40-hydrogenated castor oil | 0.1 |
| Perfume | 0.2 |
| Dimethyl ether | 33.0 |
| Water | ad 100.0 |

Formulation Example 6

| (Hair gel) | % by wt. |
| --- | --- |
| Organopolysiloxane | 2.0 |
| Polyvinyl pyrrolidone (Luviskol ® K30) | 1.0 |
| Polyacrylic acid (Carbomer) | 1.0 |
| Sodium hydroxide | 0.4 |
| PEG-35-hydrogenated castor oil | 0.1 |
| Perfume | 0.2 |
| Water | ad 100.0 |

Formulation Example 7

| (Hair gel) | % by wt. |
| --- | --- |
| Organopolysiloxane | 1.5 |
| Oleth-3-phosphate | 16.0 |
| Highly viscous mineral oil | 14.0 |
| Glycerol | 0.5 |
| Potassium hydroxide | 1.4 |
| Perfume | 0.2 |
| Water | ad 100.0 |

Formulation Example 8
(Hair Shampoo)

| (Hair shampoo) | % by wt. |
| --- | --- |
| Laurylpolyoxyethylene sulfate triethanol-amine salt (40 wt. % aq. solution) (Emul 20C, manufactured by Kao) | 32.0 |
| Lauroyl diethanolamide | 4.0 |
| Polyethylene glycol (PEG 6000, manufactured by Sanyo Chemical Industries) | 1.0 |
| Organopolysiloxane | 1.0 |
| Perfume | trace |
| Purified water | ad. 100.0 |

Formulation Example 9

| (Hair rinse) | % by wt. |
|---|---|
| Stearyltrimethylammonium chloride | 2.0 |
| Organopolysiloxane | 1.0 |
| Cetyl alcohol | 2.0 |
| Perfume | trace |
| Purified water | ad. 100.0 |

Formulation Example 10

| (Set lotion) | % by wt. |
|---|---|
| Organopolysiloxane | 1.0 |
| Perfume | trace |
| Purified water | 10.0 |
| Ethanol | ad. 100.0 |

Example 6

| (Pump foam spray) | % by wt. |
|---|---|
| Organopolysiloxane C | 5.0 |
| Polyquaternium-46 | 3.0 |
| Vinyl pyrrolidone/vinyl acetate copolymer (Luviskol ® VA64) | 2.0 |
| Cetrimonium chloiride | 1.0 |
| PEG-40-hydrogenated castor oil | 0.1 |
| Perfume | 0.2 |
| Water | ad. 100.0 |

An identical example 6A was prepared, which, however, contained an organopolysiloxane, where the proportion of the organopolysiloxane segment (a) to the poly(N-acyl alkyleneimine) segment was 51 to 49.

A comparison of the properties of both products is shown in the following table.

TABLE

| Composition according to | Example 6 | Example 6A |
|---|---|---|
| Appearance | Transparent solution | Turbid, insoluble deposit |
| Stability | No flocculation after six months storage at 40° C. | Intensive flocculation after one day |
| Feeling of hair after application | Soft | Rough due to insoluble deposit |
| Application | Good, valve not clogged | Valve clogged after several operations of the pump |

What is claimed is:

1. An aqueous dispersion comprising:
   i) an organopolysiloxane composed of an organopolysiloxane segment and a poly(N-acylalkyleneimine) segment which is bonded to at least one silicon atom of said organopolysiloxane segment via an alklene group containing heteroatom(s) and which consists of repeating units represented by formula (1):

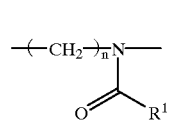

(1)

wherein $R^1$ represents a hydrogen atom or an alkyl group having 1 to 3 carbon atoms; and n is a number of 2 or 3;
   wherein the weight ratio of the organopolysioloxane segment (a) to the poly(N-acylalkyleneimine) segment (b) is at least 25/75 and less than 40/60, and the weight average molecular weight is from 10,000 to 500,000;
   ii) water.

2. The aqueous dispersion of claim 1 wherein said alkylene group containing heteroatom(s) is an alkylene group having from 2 to 20 carbon atoms and containing, between carbon atoms in the alkylene chain, at the end thereof or in the alkylene chain and at the end thereof, a group of (i) a secondary amine or a tertiary amine; (ii) an ammonium salt formed by adding $H^+$ to a secondary or tertiary amine; (iii) a quaternary ammonium salt; (iv) an oxygen atom; (v) a sulfur atom or a mixture thereof.

3. A hair care product comprising
   A) an aqueous dispersion comprising:
   i) an organopolysiloxane composed of an organopolysiloxane segment and a poly(N-acylalkyleneimine) segment which is bonded to at least one silicon atom of said organopolysiloxane segment via an alkylene group containing heteroatom(s) and which consists of repeating units represented by formula (1):

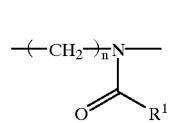

(1)

wherein $R^1$ represents a hydrogen atom or an alkyl group having 1 to 3 carbon atoms; and n is a number of 2 or 3;
   wherein the weight ratio of the organopolysiloxane segment (a) to the poly(N-acylalkyleneimine) segment (b) is at least 25/75 and less than 40/60, and the weight average molecular weight is from 10,000 to 500,000; and
   ii) water; and
   B) an ionic polymer.

4. The hair care product as claimed in claim 3, which is an aqueous aerosol foaming composition.

5. The hair care product of claim 3, wherein said organopolysiloxane has a weight-average molecular weight of from 20,000 to 200,000.

6. The aqueous dispersion of claim 1, wherein said organopolysiloxane has a weight-average molecular weight of from 20,000 to 200,000.

* * * * *